(12) United States Patent
Holland et al.

(10) Patent No.: US 10,561,798 B2
(45) Date of Patent: Feb. 18, 2020

(54) INJECTION DEVICE WITH FEEDBACK MECHANISM

(71) Applicant: OWEN MUMFORD LIMITED, Oxford (GB)

(72) Inventors: Damian Holland, Oxfordshire (GB); Oliver Gould, Oxfordshire (GB); Timothy Muller, Oxfordshire (GB)

(73) Assignee: OWEN MUMFORD LIMITED, Oxfordshire (GB)

( * ) Notice: Subject to any disclaimer, the term of this patent is extended or adjusted under 35 U.S.C. 154(b) by 432 days.

(21) Appl. No.: 15/504,406

(22) PCT Filed: Aug. 20, 2015

(86) PCT No.: PCT/GB2015/052424
§ 371 (c)(1),
(2) Date: Feb. 16, 2017

(87) PCT Pub. No.: WO2016/027096
PCT Pub. Date: Feb. 25, 2016

(65) Prior Publication Data
US 2017/0232201 A1    Aug. 17, 2017

(30) Foreign Application Priority Data
Aug. 20, 2014    (GB) .................................. 1414798.7

(51) Int. Cl.
*A61M 5/315*   (2006.01)
*A61M 5/31*    (2006.01)
*A61M 5/20*    (2006.01)

(52) U.S. Cl.
CPC ............ *A61M 5/3157* (2013.01); *A61M 5/20* (2013.01); *A61M 5/2033* (2013.01);
(Continued)

(58) Field of Classification Search
CPC .... A61M 5/20; A61M 5/2033; A61M 5/3157; A61M 5/3129; A61M 5/31511;
(Continued)

(56) References Cited

U.S. PATENT DOCUMENTS 3,660,037 A    5/1972    Sokol
6,086,568 A    7/2000    Caizza
(Continued)

FOREIGN PATENT DOCUMENTS

CN    102307606    1/2012
CN    103143082    6/2013
(Continued)

OTHER PUBLICATIONS

Chinese Office Action Application No. 2015800442796 dated Mar. 22, 2019, with English translation provided.
(Continued)

*Primary Examiner* — Kevin C Sirmons
*Assistant Examiner* — Tezita Z Watts
(74) *Attorney, Agent, or Firm* — Young & Thompson

(57) ABSTRACT

An injection device for the delivery of medicament has an indicator for providing an activation indication. The device includes a housing; a plunger slidably mounted within the housing; an actuation mechanism configured, in use, to move the plunger forward relative to a syringe so as to express medicament from the syringe. The device also includes an indicator element responsive to the forward movement of the plunger and configured to provide an audible and/or tactile and/or visual indication when the plunger reaches or approaches its forward position. The plunger includes an elongate shaft formed of at least two telescopic sections. The actuation mechanism acts on the plunger, in use, to expand the telescopic sections and to sequentially move each of the telescopic sections forwardly (Continued)

within the housing. The indicator element is arranged to be responsive to the forward movement of the trailing telescopic section.

19 Claims, 5 Drawing Sheets

(52) U.S. Cl.
CPC ...... *A61M 5/3129* (2013.01); *A61M 5/31511* (2013.01); *A61M 5/31576* (2013.01); *A61M 2005/31518* (2013.01); *A61M 2205/581* (2013.01); *A61M 2205/582* (2013.01); *A61M 2205/583* (2013.01)

(58) Field of Classification Search
CPC .... A61M 5/31576; A61M 2005/31518; A61M 2205/581; A61M 2205/582; A61M 2205/583; A61M 5/2422
See application file for complete search history.

(56) References Cited

U.S. PATENT DOCUMENTS

| | | | |
|---|---|---|---|
| 8,043,262 B2* | 10/2011 | Streit | A61M 5/2033 604/137 |
| 8,046,262 B1* | 10/2011 | Antony | G06Q 10/08 705/26.1 |
| 9,186,459 B2* | 11/2015 | Bechmann | A61M 5/2033 |
| 2009/0259195 A1 | 10/2009 | Lin Lee | |
| 2012/0220954 A1* | 8/2012 | Cowe | A61M 5/2033 604/228 |
| 2013/0324939 A1 | 12/2013 | Brereton et al. | |

FOREIGN PATENT DOCUMENTS

| | | |
|---|---|---|
| EP | 2 140 897 A1 | 1/2010 |
| EP | 2 583 705 A1 | 4/2013 |
| WO | 95/35126 A1 | 12/1995 |
| WO | 2010/035056 A1 | 4/2010 |
| WO | 2010/089308 | 8/2010 |
| WO | 2011/123024 | 10/2011 |
| WO | 2012/049484 A2 | 4/2012 |

OTHER PUBLICATIONS

European Examination Report for Application No. 15 771 216.7 dated Feb. 14, 2019.
International Search Report, dated Dec. 14, 2015, from corresponding PCT application.
GB Search Report, dated Feb. 24, 2015, from corresponding GB application.

* cited by examiner

INJECTION DEVICE WITH FEEDBACK MECHANISM

FIELD OF THE INVENTION

This invention relates to injection devices including an activation indicator and in particular, but not exclusively to an injection device having an end of dose indication.

BACKGROUND OF THE INVENTION

Injection devices are used for the convenient administration of medicaments. For example, auto injectors may be used for providing a single metered dose of a medicament, such as Epinephrine, in an emergency or for providing regular metered doses of a medicament, such as insulin. An example of one such injection device is shown in the applicant's co-pending application PCT/GB2011/051950. Such injectors typically comprise a housing within which is housed (or defined) a syringe or cartridge containing medicament. For simplicity the present application uses the term "syringe" but it will be appreciated that this is used in a non-limiting manner and is intended to encompass cartridges and/or other arrangements which may be either discrete or integral to the housing. The housing generally includes an actuation mechanism which may be of any convenient form and is arranged to move a plunger between an initial rearward, position and, a forward, delivery position so as to express medicament from the syringe.

It is known to provide such injection devices with an activation indicator which provides one or more of a visual, tactile or audible indication of the firing of the injector actuation mechanism. In particular since the delivery of a desired dose of medicament may take a certain amount of time after the user activates the injector (particularly for example, with high viscosity drugs or small needle diameters) it is useful to provide an injection complete indication. The term "Injection Complete" (or "injection completion") is used to refer to a condition in which a satisfactory delivery of the medicament has been achieved.

It is desirable for auto injectors to be of a compact form so that they can be carried around and used unobtrusively (typically such auto injectors are provided in a pen injector type form). Further compact injectors may be simple to manufacture, assemble and use with consequent savings in manufacturing and assembly costs, and a lower environmental impact. Accordingly, any activation indicator provided within the injector must be of compact form and not significantly impact the overall size of the injection device.

Embodiments of the present invention are intended to address at least some of the abovementioned problems.

SUMMARY OF THE INVENTION

Accordingly, in one aspect, the present invention provides an injection device for the delivery of medicament and having an indicator for providing an activation indication, the device comprising:
  a housing;
  a plunger slidably mounted within the housing;
  an actuation mechanism configured, in use, to move the plunger forward relative to the syringe so as to express medicament from the syringe; and
  an indicator element responsive to the forward movement of the plunger and configured to provide at least one of an audible, tactile or visual indication when the plunger reaches or approaches its forward position; and characterised in that the plunger comprises an elongate shaft formed of at least two telescopic sections;
  the actuation mechanism acts on the plunger, in use, to expand the telescopic sections and to sequentially move each of the telescopic sections forwardly within the housing; and wherein
  the indicator element is arranged to be responsive to the forward movement of the trailing telescopic section.

Telescopic as used herein is intended to refer to elongate interconnected sections which are relatively moveable in the axial direction such that the overall axial length of the plunger may be extended (for example the sections may slide relative to one another). In other words, the telescopic sections enable the shaft to be expanded between a collapsed (or nested) configuration in which the sections substantially overlap and an expanded configuration in which the length of the plunger shaft is extended. The interconnection between the sections may allow relative axial movement between the sections but may provide a stop or limit to the relative axial movement between the sections (so as to limit the movement beyond a predetermined extent and maintain the integrity of the shaft).

In the context of the invention the sequential movement of the plunger sections should be understood to mean that each of the sections move during the operation sequence of the device. The particular order of movement of the sections may depend upon the particular embodiment of the invention. The skilled person will appreciate that during the actuation movement of the plunger the movement/expansion of the plunger sections may involve a degree of compound movement. For example at least some sections of the plunger may move together for at least a portion of the activation. In other words, through the full actuation movement the plunger sections may each move relative to the housing (to provide the required forward movement of the syringe plunger) and may move relative to one another (to provide the expansion of the plunger) but the particular order of the movement during any portion of the activation is not considered essential to the invention.

Typically, the indicator may be arranged to provide an injection completion indication and as such may be configured to be responsive to arrival of the plunger at or near its fowardmost position (at which position the medicament will have been fully dispensed).

Advantageously, the provision of a telescopic plunger provides a convenient and compact means of activating the indicator element. In particular, it will be appreciated that the length of the telescopic plunger can be easily adjusted in order to provide the desired timing of the indicator element response when producing an injection device in accordance with an embodiment of the invention.

The indicator element may be biased towards its indicating position. The plunger may be arranged such that when the plunger is in its rearward position (i.e. the starting or pre-firing position) the plunger holds the indicator element against said bias. For example, the trailing telescopic section of the plunger may be arranged to hold the indicator element.

Release of the indicator element (in response to the forward movement of the plunger) may be arranged to enable said indicator element to move under its bias. The movement of the indicator element may be arranged to create a kinetic impact resulting in an audible and/or tactile indication. For example, the indicator element may strike a percussive surface which may, for example, be associated with the housing of the injection device. Alternatively, the indicator element may include opposing members which are arranged to strike one another to provide the kinetic impact. In some embodiments, the housing may be provided with a window to allow the indicator element to be viewed externally. For example, the window may be aligned with the indicator element such that the indicator element may move into or out of alignment with the window during movement under said bias so as to provide a visual indication.

The indicator element may comprise one or more resilient members. The, or each, resilient member may be held in a stressed position (i.e. against its own bias) when the plunger is in its rearward position. For example, the indicator element may comprise a spring clip. The spring clip may be configured to snap together when released from its stressed position to provide the audible and/or tactile indication. The clip may, for example, be formed from a sheet metal pressing. The spring clip may comprise two opposing jaws connected by a resilient spring section. The plunger may hold the jaws of the spring clip apart so as that the spring clip is deformed and in a stressed position.

The trailing telescopic section of the plunger may at least partially radially surround at least one other telescopic section. Thus, the trailing telescopic section of the plunger may be the section having the greatest radial width so as to hold the resilient indicator element at its maximum deflection until the indicator is released to provide an indication.

Alternatively, the trailing telescopic member of the plunger may be at least partially surrounded by at least one other telescopic section. Thus, one or more of the leading telescopic sections may be the section having the greatest radial width so as to reduce the stressed position of the resilient member gradually or in stages during extension of the telescopic element. Reduction in the stressed position of the resilient member gradually or in stages may be arranged to provide indication of injection action.

Alternatively, the indicator element may comprise a shuttle member. The shuttle member may be arranged for generally transverse movement under the indicator bias. For example, the shuttle member may be disposed in a generally transverse passageway. The transverse passageway may, for example, be formed in the housing (for example, within the trigger button) of the injection device. The shuttle member may be moveable along the length of the transverse passageway. The indication position of the shuttle member may be at, or proximal to, one end of the passageway. The shuttle member may be biased towards the indicating position along the length of the transverse passageway.

The plunger may be arranged, in its rearward position, to lock the indicator element against said bias in a position which is spaced away from said end of the passageway. In such embodiments, the trailing telescopic section of the plunger may be at least partially surrounded by at least one of the other telescopic sections. In these embodiments, the trailing telescopic section need only latch or block the shuttle member within the passageway and does not need a substantial radial width. The axis of the plunger may be perpendicular to the transverse passageway and an aperture may be provided aligned with the plunger through which the tip of the trailing telescopic section may extend when the plunger is in the rearward position.

The actuation mechanism may comprise a drive source and a latch arranged to hold the plunger in a rearward position. As such, the rearward position of the plunger may be a cocked position of the actuation mechanism. The injection device may further comprise a trigger (which may be associated with the housing) arranged to release the latch. On release of the latch, the plunger is able to move forward under the influence of the drive source. Thus, the drive source may act to expand the telescopic sections and sequentially move each of the telescopic sections forwardly within the housing.

In some embodiments the drive source may simply be a spring such as a compression spring. In a particular embodiment the actuation mechanism comprises an intermediate drive member. The drive source may, therefore, comprise a first drive spring disposed between the intermediate drive member and the housing (or a part associated therewith) and a second compression spring disposed between the intermediate drive member and the plunger. In such an arrangement, upon release of the latch the drive springs urge the intermediate drive member and plunger forwardly (and may act in a compound motion). The second compression spring may act upon a rearward facing flange surface formed at the forwardmost end of the telescopic plunger.

The indicator element may be provided on the intermediate drive member. For example, the indicator element may be connected to the intermediate drive member such that it is moveable relative to the housing but, during activation, does not slide forwardly to the same extent as the leading portion of the plunger. In particular, the indicator element may comprise a spring clip connected to a rear surface of the intermediate drive member.

The leading telescopic plunger section may comprise an abutment surface configured to be releasably engaged by a latch of the actuation mechanism. The abutment surface may be formed at the rearward end of the leading telescopic plunger section. The abutment surface may, for example, be formed by the neck of a head provided at the rearward tip of the leading telescopic plunger section. When the plunger is in its fully collapsed configuration, the abutment surface may be at, or proximal to, the rearward end of the plunger.

According to a further aspect, the present invention provides a plunger for an injection device, the plunger comprising an elongate shaft formed of at least two telescopic sections, said telescopic sections being arranged to axially extend the plunger shaft during actuation of the injection device and wherein the leading telescopic section includes at least one abutment surface configured to be releasably engaged by a latch of the injection device.

The forward end of the leading plunger section may be arranged to engage a syringe or cartridge of the injection device. The forward end may be provided with a rearward facing flange surface for engagement with the actuation mechanism. For example, the forward end of the drive source (for example, the drive spring) may engage the rearward facing flange surface. The forward end of the leading plunger section may be arranged to co-operate with a piston or bung of the syringe.

The plunger may comprise a trailing section and an intermediate section disposed between the leading and trailing sections.

Whilst the invention has been described above, it extends to any inventive combination set out above, or in the following description or drawings.

BRIEF DESCRIPTION OF THE DRAWINGS

The invention may be performed in various ways, and embodiments thereof will now be described by way of example only, reference being made to the accompanying schematic drawings, in which.

DETAILED DESCRIPTION OF EMBODIMENTS

"Front" as used herein will be understood to refer to the end of the injector assembly (or components thereof) which, in use, is closest to the delivery needle delivery end of the injector (i.e. the end which is pointed at the skin). "Rear" as used herein will be understood to refer to the end of the injector assembly (or components thereof) which, in use, is furthest from the delivery needle end of the injector (i.e. the end which is pointed away from the skin). "Forward" and "rearward" will, likewise, be understood to refer to the directions orientated towards the front and rear of the injector assembly. Thus, it will be appreciated that the forward direction is generally the actuation direction of the device (although in some devices there may be some steps of the actuation, for example a needle withdrawal, which are in the rearward direction). The terms "leading" is used herein to conveniently refer to the sections of the plunger which lead during actuation movement, for example in that they either move forward first sequentially or move forward to the forwardmost position. Likewise "trailing" will be understood to refer to the sections which are rearmost during or after actuation.

For convenience the preferred embodiment is shown in an injector device substantially of the type disclosed in the applicants co-pending International Patent Application No. PCT/GB2011/051950 (the contents of which is incorporated herein by reference). It will however be appreciated that the invention is not limited to such an arrangement and may be used in injectors having other actuation arrangements.

An injection device 1 according to an embodiment comprises a housing 10 having a generally elongate and cylindrical form within which is housed a syringe 20. The rear portion of housing 10 includes an actuation mechanism 30 which may be of any convenient form. The forward end of the injector device is omitted in FIG. 1 for clarity and the skilled person will appreciate that it will typically comprise a forward section of the housing 10 which encloses the syringe 20 and the needle at the forward end of the syringe. The forward section of the housing may also include a cap and/or a needle shield arrangement as are known in the art.

Figure 1A:
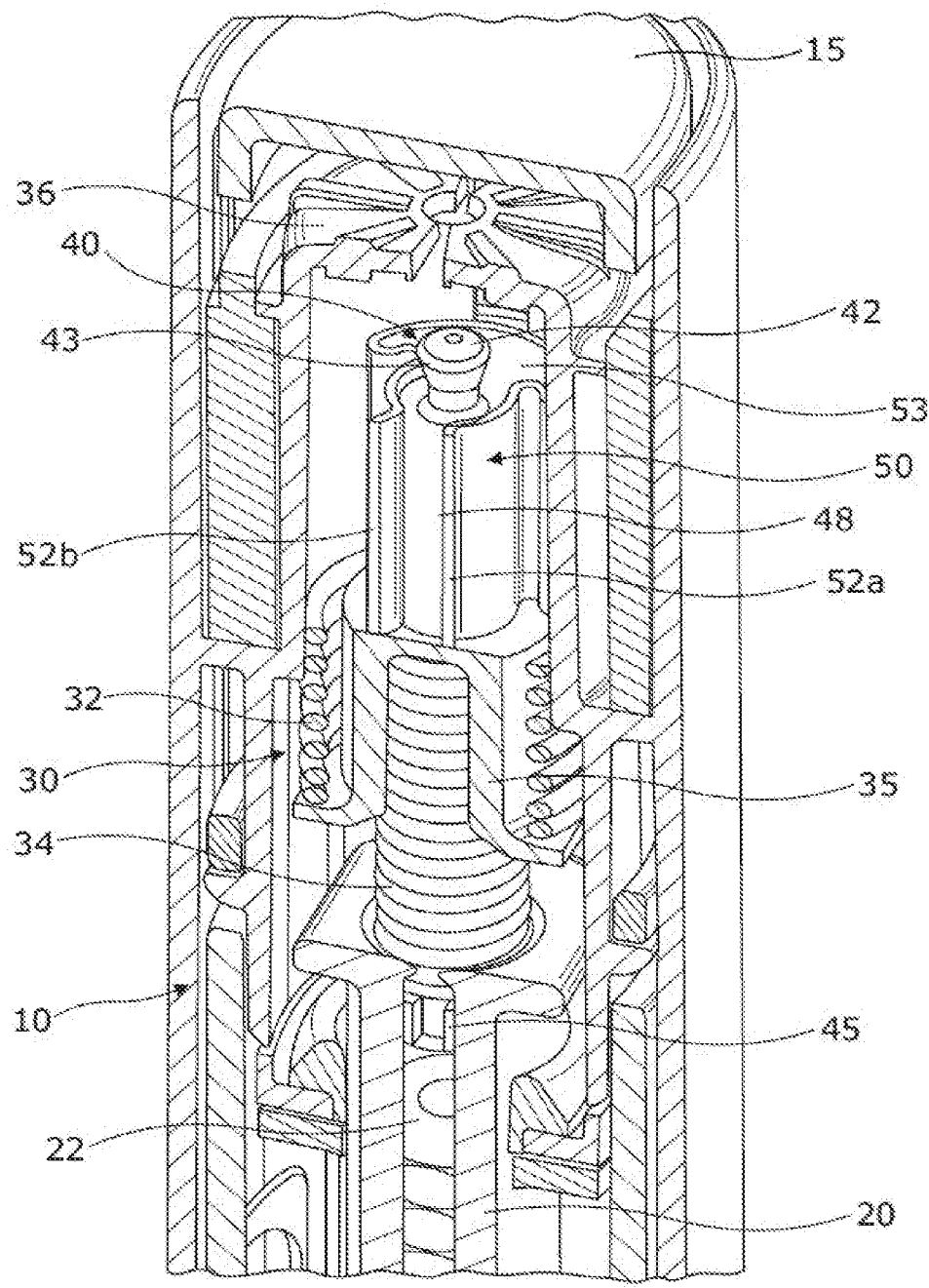
FIG. 1 is a three-dimensional partial cross sectional view of the rear section of an autoinjector in accordance with a first embodiment of the invention.
Figure 1B:
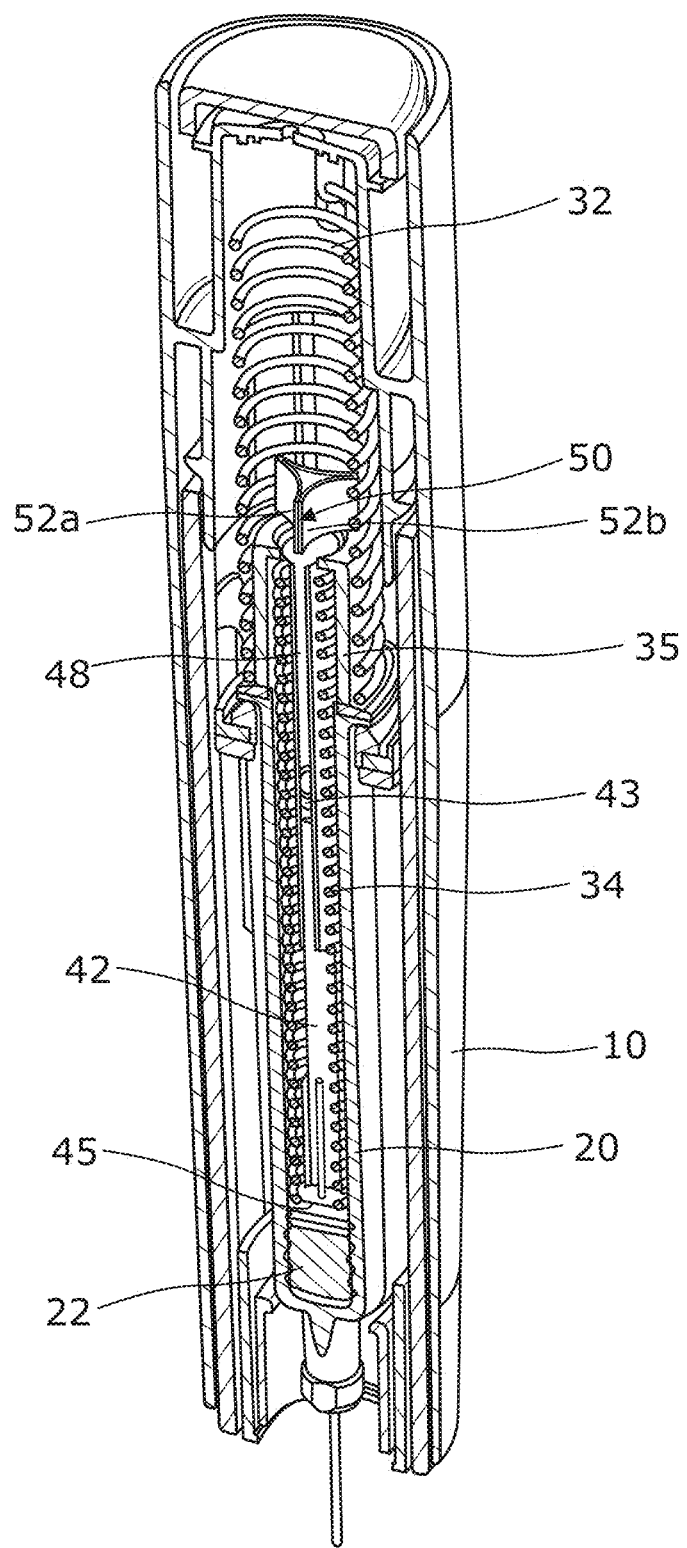

The actuation mechanism 30 is arranged to move a plunger 40 between an initial rearward position, as shown in FIG. 1a, and a forward delivery position, as shown in FIG. 1b, such that the plunger 40 may express a dose from the syringe 20 by moving the bung or piston 22 of the syringe forward within the syringe body. In the illustrated embodiment the actuation mechanism 30 is of the type which initially moves the syringe 20 forward from within the housing 10 such that the needle of the syringe may automatically penetrate the skin and then subsequently continues to move the plunger relative to the syringe to express the entire dose of medicament from within the syringe 20. As mentioned above, the present invention is not limited to any particular actuation mechanism and it will, therefore, be appreciated that other injector arrangements are known in which the needle protrudes from the housing prior to firing such that it is manually inserted into the skin (and the syringe may be fixed relative to the housing). As explained further below, the actuation mechanism 30 includes a drive source in the form of at least one compression spring 32, 34 for urging the plunger 40 and a latch 36 which initially holds the plunger in its rearward position against the force of the spring 32, 34. A trigger button 15 is provided associated with the housing 10 and is arranged in use to release the plunger 40 from the latch 36 to free it for forward movement.

It may be noted that the embodiment of FIG. 1 includes an actuation mechanism 30 of the type which includes a first drive spring 32, which extends between an intermediate member 35 and a surface associated with the housing 10, and a second drive spring 34, which extends between the intermediate member 35 and a flange 45 having a rearward facing abutment surface, for receiving the spring 34 which is formed at the forward end of the plunger 40. The flange 45 has a rearward facing abutment surface for receiving the spring 34. For the purposes of clarity it may be noted that the first drive spring 32 is only partially shown in FIG. 1a and would typically extend rearwardly to the forward facing inner surface of the latch 36 (or some other engagement feature associated with the housing). In FIG. 1a, the injection device is shown in a position in which a trigger button 15 has already been depressed forwardly towards the inside of the housing 10 and has caused the head 43 of the plunger 40 to be released from the latch 36. In the position shown, the first drive spring 32 has begun to expand and has resulted in forward movement of the intermediate member 35, plunger 40 and indicator 50. As the illustrated arrangement is of a type in which the syringe 20 initially moves forward, the plunger 40 initially presses upon the bung or piston 22 of the syringe but due to the substantially incompressible nature of the medicament contained within the syringe 20, the piston 22 does not move relative to the syringe 20 until the syringe 20 has moved to a forward position and reached a stop.

It may be noted that during the initial movement shown in FIG. 1a the plunger 40 is in its collapsed configuration with the leading plunger section 42 positioned within the trailing plunger section 48. In this embodiment the telescopic plunger sections are generally concentric. As the forward movement of the plunger 40 continues under the force of the drive springs 32, 34 the inner plunger section 42 will begin to move forward of the outer plunger section 48. Once the inner leading plunger section 42 has slid to its fully telescopically extended position relative to the outer plunger 48 the interconnection between the plunger shaft sections will require the trailing outer plunger 48 to also be drawn forwardly along with the leading section 42. Thus, the plunger sections 42, 48 both extend and move sequentially forward under the force of the drive springs 32, 34 as part of the plunger actuation movement to drive the piston 22 of the syringe 20 fully forward, to the position shown in FIG. 1b.

At the rear of the intermediate member 35 there is provided an indicator 50 in the form of a pressed metal spring clip which comprises a pair of opposed jaws 52a and 52b connected by a sprung body section 53. Initially, when the plunger 40 is in the rearward position, the telescopic shaft of the plunger 40, and particularly the trailing outer plunger section 48 is positioned between the jaws 52a, 52b of the spring clip 50 as shown in FIG. 1a. Thus, the plunger 40 holds the jaws 52a and 52b apart in a deformed position against their resilient spring bias.

As shown in FIG. 1b, when the plunger 40 reaches the desired forward position (which would typically be as the piston 22 reaches the forward end of the syringe 20 so that a full dose of medicament has been dispensed) the trailing outer plunger section 48 moves forward of the forwardmost extend of the spring clip 50 (i.e. beyond the rearmost extent of the intermediate member 35) freeing the sprung clip 50 to move back to its undeformed closed position. This closure occurs in a snapping manner resulting in the jaws 52a and 52b impacting one another so as to create an audible (and optionally tactile) indication that the plunger 40 has reached a predetermined forward position.

In an alternative arrangement, the indicator 50 may be replaced with an indicator member which is held against a bias by the rearward end of the plunger 40 and released when the rearmost end of the trailing section of the plunger 48 moves forward. Such an arrangement may use a substantively identical actuation mechanism as that shown in FIG. 1. An indicator arrangement for such an embodiment is shown in an exploded view in FIG. 2. Conveniently, the indicator 250 is formed within the trigger 215 of the injection device. The trigger 215 comprises a body 215b and a cover 215a which together define an inner space within which the indicator 250 is provided. A transverse channel 252 is defined within the trigger 215 extending substantially across the full width of the trigger 215. A shuttle member 254 is slideably received within the aperture 252 and is provided with a spring 251 which is arranged to bias the shuttle 254 towards an indication position at one end of the passageway (the right hand side as shown in the Figures). An aperture 253 is formed in the forward side of the transverse channel 252. The rearward end of the trailing plunger section 48 is configured to project rearwardly through the aperture 253 when the plunger 40 is in its rearward position. A corresponding aperture 255 is also formed in the shuttle 254 through which the plunger 40 also extends so as to latch the shuttle 254 away from the indicating position and to hold the spring 251 in a compressed position. It will, however, be appreciated that the plunger end could alternatively lock the transverse channel 252 in front of the shuttle 254 such that an aperture 255 would not be required.

Figure 2:
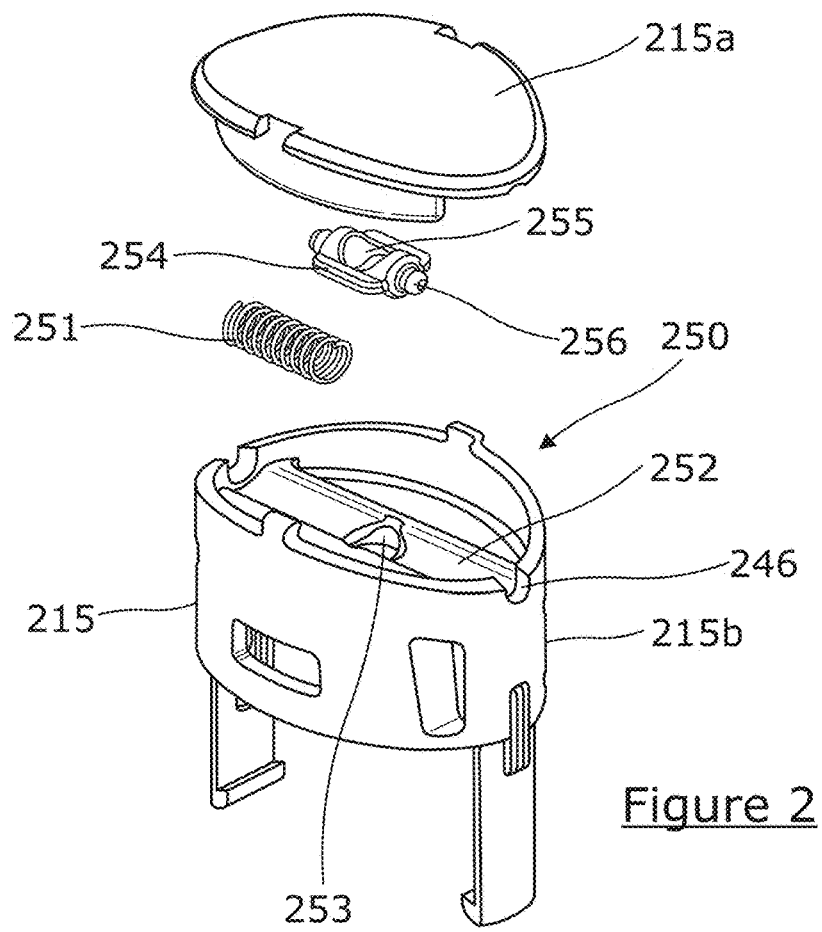
FIG. 2 is an exploded three-dimensional view of an indicator element for use in a second embodiment of the invention.
Figure 3A:
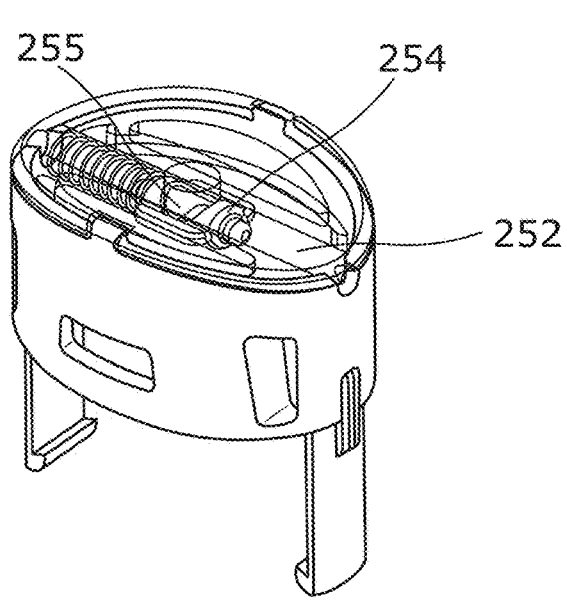
FIG. 3 are three-dimensional views showing the operation of the indicator element of FIG. 2.
Figure 3B:
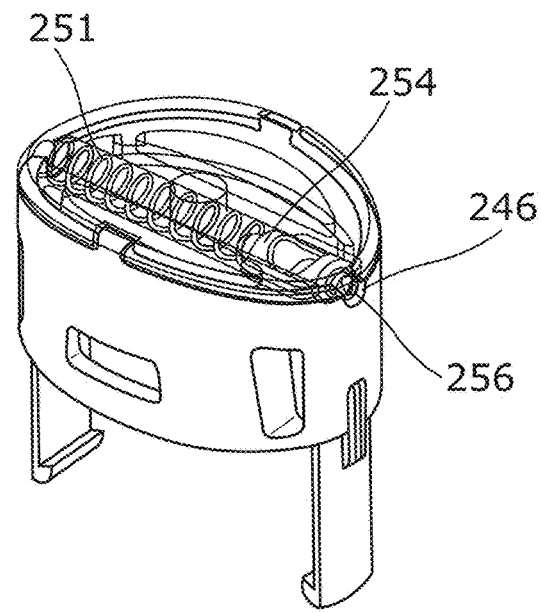

The operation of the indicator 250 of FIG. 2 is illustrated in FIG. 3. FIG. 3a shows the shuttle 254 in its retracted position with the aperture 255 aligned with the aperture 253 of the transverse channel 252. In this position the end of the trailing plunger section 48 would extend through the apertures and latch the shuttle 254. When the plunger 40 moves forward during actuation of the injection device the plunger 40 would be moved forwardly in the same manner as described above (with reference to the embodiment of FIG. 1) until the trailing section 48 was moved forward out of the apertures 255 and 253. Thus, the shuttle 254 would be free to move to the position shown in FIG. 3b. The spring 251 would be selected to be sufficiently strong that the shuttle 254 would strike the end wall of the transverse channel 252 to create an audible and/or tactile indication. As the indicator 250 is formed in the trigger button 215 the users thumb would typically be positioned on the cover 215a throughout operation of the injector device and would be particularly receptive to a tactile indication provided within the trigger button 215. It may be noted that the trigger 215 is also provided with a window 246 in its sidewall and the shuttle 254 is provided with a correspondingly dimension projection 256 which in the indication position enters the window 246. Thus, the indicator 250 may also provide a visual indication.

Figure 4:
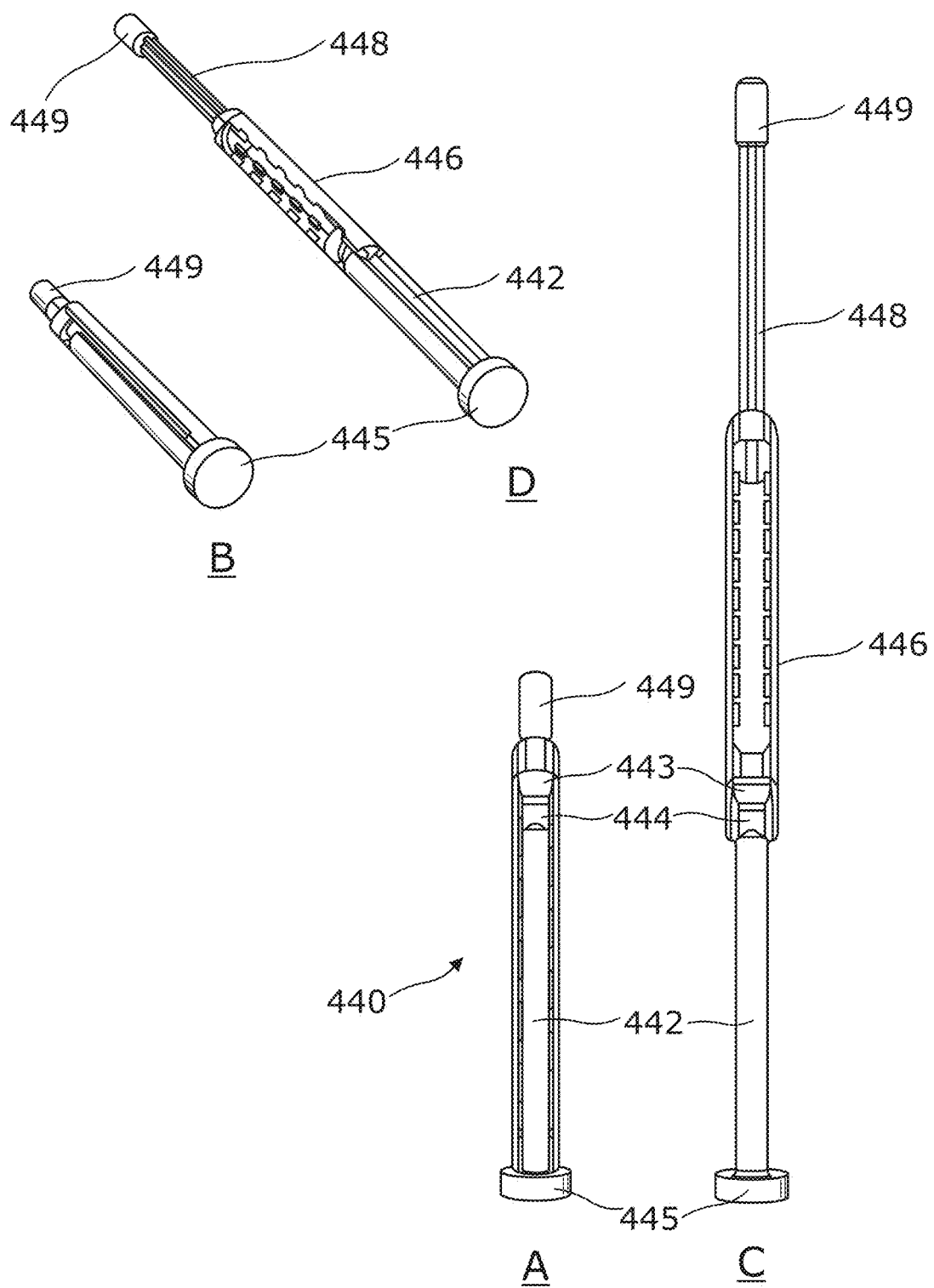
FIG. 4 shows three-dimensional views and side-views of a plunger for use in embodiments in both a nested and expanded configuration.

A telescopic plunger arrangement 440 for use in embodiments of the invention (and particularly suitable for use with the indicator 250 of FIGS. 2 and 3) is shown in FIG. 4. FIGS. 4a and 4b show the plunger 440 in a collapsed configuration and FIGS. 4c and 4d show the plunger 440 in its expanded configuration. The plunger 440 extends from a flange 445 at its forward end which is arranged to engage the piston of a syringe with its forward face and be driven forward by an actuation mechanism using its rearwardly facing flange surface. In the collapsed state the plunger 440 is provided with a tip 449 at its rearmost end which may be used to engage the indicator (such as the shuttle 254 via the apertures 253 and 255).

The rearward end of the plunger 440 is provided with an enlarged head 443 which is positioned rearwardly of a neck defining an abutment surface 444 for engagement with a latch of the actuation mechanism 30. As seen most clearly from the expanded configuration of the plunger 440 the plunger comprises three slideably connected telescopic sections namely a leading section 442, a trailing section 448 and an intermediate connecting section 446. It will be noted that the tip 449 is formed on the trailing section 448 and the flange 445 and head 443 (including the abutment surface 444) are all formed on the leading section 442. Thus, it will be appreciated that, in the latched position, the load of the actuation mechanism is held between the abutment surface 444 and the flange 445. Upon release of the latch the leading section 442 and intermediate section 446 may slide relative to the trailing section 448 so that the plunger may expand to approximately triple its collapsed length of the plunger before the tip 449 of the trailing portion is moved out of engagement with the indicator 250.

Figure 5:
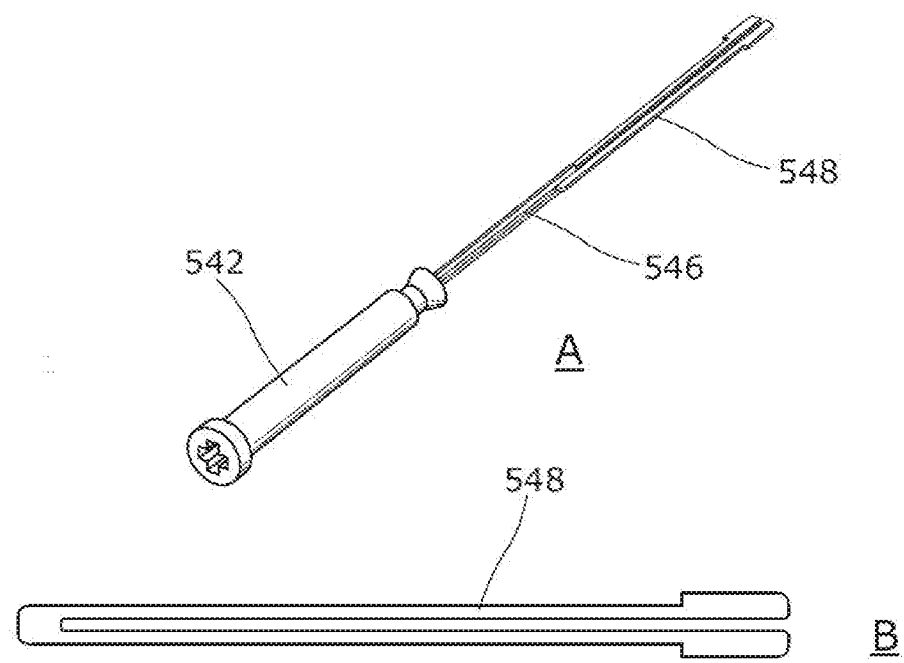
FIG. 5 shows an alternate plunger arrangement in accordance with an embodiment.

In the embodiment of FIG. 4 each of the sections 442, 446, 448 of the plunger 440 are formed of moulded plastic parts. FIG. 5 illustrates an alternative embodiment in which the intermediate 546 and trailing 548 telescopic sections are formed from flat, substantial U shaped elongate members. For example, the members may be conveniently formed from stamped metal pressings. The profile of one of the pressings is shown in FIG. 5b. It will be seen that the sections 546 and 548 may be simply interconnected by being slotted together and positioned such that they lie in perpendicular planes. Thus, the leading section 542 which remains formed of a moulded plastic part is provided with an X shaped internal profile into which the intermediate 546 and trailing 548 sections may slide.

Figure 6:
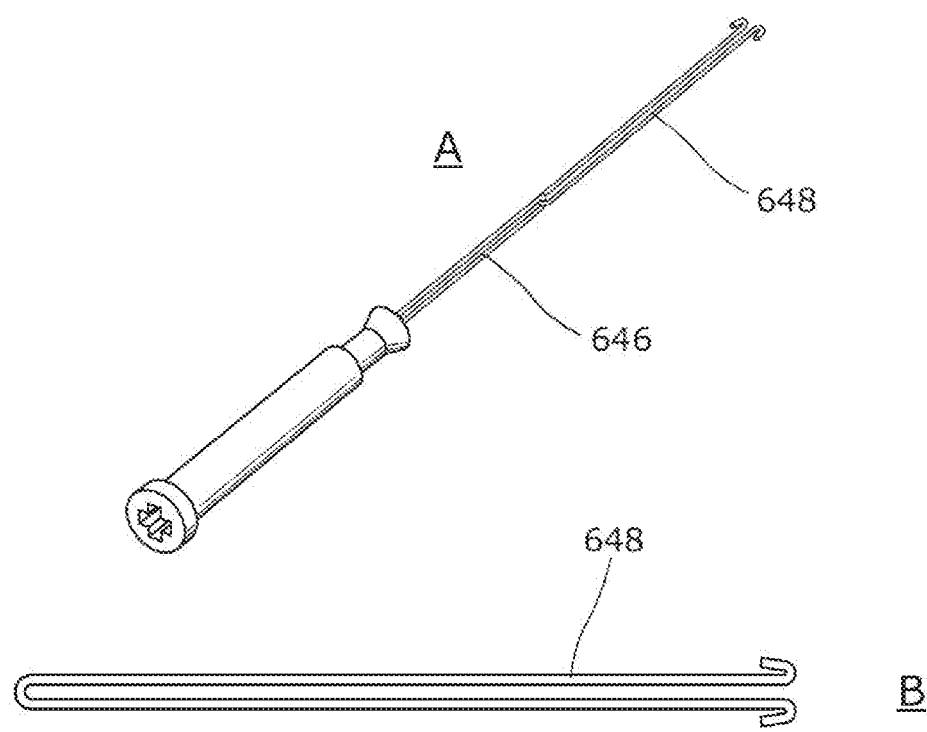
FIG. 6 shows a further alternate plunger arrangement in accordance with an embodiment.

Alternatively, as shown in FIG. 6, the intermediate 646 and trailing 648 sections may be formed from shaped tubular sections such as metal wire forms. The profile of each section is as show in FIG. 6b.

Although the invention has been described above with reference to the preferred embodiments, it will be appreciated that various changes or modifications may be made without departing from the scope of the invention as defined in the appended claims. In some embodiments the device may be a single use device and, for example, the syringe may be integrally formed with the housing.

Whilst the embodiments described above utilise a kinetic impact to create an indication it will be appreciated that numerous other forms of indication could be used as an additional or alternative indication in response to movement of the trailing portion of the plunger. For example rather than kinetic impact any form of energy could be utilised to create a noise, for example chemical, electrical, fluidic, pneumatic, etc. could all be derived from the motion of the indicator. In some embodiments an electrical signal could be triggered by movement of the plunger to, for example, activate an electronic sounder.

The invention claimed is:

1. An injection device for the delivery of medicament, the device comprising:

a housing;

a plunger slidably mounted within the housing; and an actuation mechanism configured, in use, to move the plunger forward relative to a syringe so as to express medicament from the syringe; and an indicator for providing an activation indication, the indicator being responsive to the forward movement of the plunger and configured to provide an audible and/or tactile and/or visual indication when the plunger reaches or approaches a forward position;

wherein:

the plunger comprises an elongate shaft formed of at least two telescopic sections;

the actuation mechanism acts on the plunger, in use, to expand the plunger forwardly by moving each of the at least two telescopic sections relative to each other and to sequentially move each of the at least two telescopic sections forwardly within the housing; and wherein the indicator is arranged to be responsive to a forward movement of a trailing telescopic section.

2. The injection device as claimed in claim 1, wherein the indicator is biased towards an indicating position and, in a rearward position, the plunger is arranged to hold the indicator against a bias of the indicator.

3. The injection device as claimed in claim 2, wherein release of said indicator enables the indicator to move under the bias of the indicator to create a kinetic impact resulting in an audible and/or tactile and/or visual indication.

4. The injection device as claimed in claim 1, wherein the housing has a window aligned with the indicator such that the indicator may move into or out of alignment with the window to provide a visual indication.

5. The injection device as claimed in claim 4, wherein the indicator comprises a resilient member and wherein, in a rearward position, the plunger holds the indicator in a stressed position.

6. The injection device as claimed in claim 5, wherein the indicator comprises a spring clip configured to snap together when released from a stressed position to provide said audible and/or tactile indication.

7. The injection device as claimed in claim 6, wherein the trailing telescopic section of the plunger at least partially radially surrounds at least one other telescopic section.

8. The injection device as claimed in claim 6, wherein the trailing telescopic section of the plunger is at least partially surrounded by at least one other telescopic section.

9. The injection device as claimed in claim 2, wherein the indicator comprises a shuttle member disposed in a generally transverse passageway, the indication position of the shuttle member being at, or proximal to, one end of the transverse passageway and the shuttle member being biased towards the indicating position along the length of the transverse passageway.

10. The injection device as claimed in claim 9, wherein the plunger is arranged, in its rearward position, to lock the indicator against said bias in a position which is spaced away from said end of the transverse passage-way.

11. The injection device as claimed in claim 10, wherein the trailing telescopic section of the plunger is at least partially radially surrounded by at least one other telescopic section.

12. The injection device as claimed in claim 1, wherein the actuation mechanism comprises a drive source and a latch arranged to hold the plunger in a rearward position against the drive source and wherein the injection device further comprises a trigger, associated with the housing, the trigger arranged to release the latch to allow the plunger to move forward under the influence of the drive source.

13. The injection device as claimed in claim 12, wherein the actuation mechanism further comprises an intermediate drive member and the drive source comprises a first compression drive spring disposed between said intermediate drive member and said housing, and a second compression spring disposed between said intermediate drive member and the plunger.

14. The injection device as claimed in claim 13, wherein the indicator is provided on the intermediate drive member.

15. The injection device as claimed in claim 12, wherein a leading telescopic section of the plunger comprises an abutment surface configured to be releasably engaged by the latch.

16. The injection device as claimed in claim 15, wherein the abutment surface is provided at or proximal to a rear end of the leading telescopic section.

17. The injection device as claimed in claim 16, wherein a forward end of the leading telescopic section is arranged to engage the syringe and is provided with a rearward facing flange surface for engagement with the actuation mechanism.

18. The injection device as claimed in claim 15, wherein the plunger further comprises an intermediate telescopic section disposed between the leading telescopic section and the trailing telescopic section, wherein the leading telescopic section, the intermediate telescopic section and the trailing telescopic section are slidably connected.

19. The injection device as claimed in claim 2, wherein the housing has a window aligned with the indicator such that the indicator may move into or out of alignment with the window to provide a visual indication.

* * * * *